(12) United States Patent
Quellet et al.

(10) Patent No.: US 10,456,338 B2
(45) Date of Patent: Oct. 29, 2019

(54) PERFUME COMPOSITION

(71) Applicant: GIVAUDAN SA, Vernier (CH)

(72) Inventors: Christian Quellet, Bienne (CH); Sandrine Le Tirilly, Paris (FR); Addi Fadel, Paris (FR); Aurelle Ferry, Attainville (FR); Isballe Abram, Asnieres sur Seine (FR)

(73) Assignee: GIVAUDAN S.A., Vernier (CH)

( * ) Notice: Subject to any disclaimer, the term of this patent is extended or adjusted under 35 U.S.C. 154(b) by 0 days.

(21) Appl. No.: 15/526,580

(22) PCT Filed: Dec. 16, 2015

(86) PCT No.: PCT/EP2015/080053
§ 371 (c)(1),
(2) Date: May 12, 2017

(87) PCT Pub. No.: WO2016/097024
PCT Pub. Date: Jun. 23, 2016

(65) Prior Publication Data
US 2017/0333302 A1    Nov. 23, 2017

(30) Foreign Application Priority Data
Dec. 16, 2014 (EP) ..................... 14198282

(51) Int. Cl.
| *A61K 8/11* | (2006.01) |
| *A61Q 13/00* | (2006.01) |
| *A61K 8/81* | (2006.01) |
| *A61K 8/898* | (2006.01) |
| *A61K 8/04* | (2006.01) |
| *C11B 9/00* | (2006.01) |

(52) U.S. Cl.
CPC ................ *A61K 8/11* (2013.01); *A61K 8/042* (2013.01); *A61K 8/044* (2013.01); *A61K 8/8147* (2013.01); *A61K 8/8152* (2013.01); *A61K 8/898* (2013.01); *A61Q 13/00* (2013.01); *C11B 9/0015* (2013.01); *A61K 2800/30* (2013.01); *A61K 2800/33* (2013.01); *A61K 2800/5424* (2013.01); *A61K 2800/5426* (2013.01)

(58) Field of Classification Search
CPC ....................................................... A61K 8/11
See application file for complete search history.

(56) References Cited

U.S. PATENT DOCUMENTS

| 2007/0149424 A1* | 6/2007 | Warr ........................ A61K 8/11 |
| | | 510/101 |
| 2014/0045949 A1* | 2/2014 | Goutayer ............. A23D 7/0053 |
| | | 514/772.6 |

FOREIGN PATENT DOCUMENTS

| GB | 2311296 A | 9/1997 |
| WO | 2014029695 A1 | 2/2014 |

OTHER PUBLICATIONS

EP Search Report for corresponding application EP 14198282.7 dated Jun. 12, 2015.
International Search Report for corresponding application PCT/EP2015/080053 dated Feb. 24, 2016.

* cited by examiner

Primary Examiner — Arrie L Reuther
(74) Attorney, Agent, or Firm — Norris McLaughlin, PA

(57) ABSTRACT

Perfume composition provided in the form of a plurality of dispersed perfume-containing droplets, suspended in an aqueous dispersing medium, said perfume droplets being mono-dispersed and having a diameter of 200 micrometers to 4000 micrometers, wherein said droplets comprise more than 60 wt %, of perfume ingredients, and wherein 25 wt or less of said perfume ingredients are linear or branched alkyl alcohols and/or alkenyl alcohols; 10 wt % or less of the perfume ingredients are aldehydes; and 10 wt % or less of the perfume ingredients have a ClogP less than 2.1.

14 Claims, No Drawings

PERFUME COMPOSITION

This is an application filed under 35 USC 371 of PCT/EP2015/080053, filed 16 Dec. 2015, which in turn was based on EP 1419828.7 filed 16 Dec. 2014. This application claims the full priority benefit to the foregoing applications and also incorporates them here by reference as if set forth herein.

This invention is concerned with perfume compositions that are provided in the form of substantially mono-dispersed, macroscopic droplets suspended in an aqueous continuous phase, and more particularly the invention is concerned with said compositions that are free of polar solvents, and/or surfactants.

Compositions formed by a micro-fluidic or milli-fluidic process and consisting of a plurality of macroscopic droplets of an internal phase dispersed in an aqueous gel continuous phase, in which the internal phase is substantially immiscible, are known in the art (see US 2014/0045949). Each of the droplets is coated with a layer of a coacervate, which essentially acts as a barrier separating the droplets of internal phase from the continuous phase, preventing coalescence of the droplets. The coacervate layer is formed by the interaction of oppositely charged coacervate precursor polymers at the interface between internal and continuous phases. A coacervate precursor polymer capable of forming a cationic charge may be a polymer, such as an amino-silicone, more particularly amodimethicone; whereas a coacervate precursor polymer capable of forming the opposite (anionic) charge can be a polyacrylic acid, also referred to as carbomer.

It is further disclosed in US 2014/0045949 that one of the phases (internal or continuous), may contain a perfuming agent. However, no significance is attached to the specific composition of the perfuming agent. In other words, according to the teaching of this document, any perfume ingredients may be employed in the droplets, without precaution.

Aqueous-based, ethanol-free perfume compositions are known in the art. Such compositions are intended as a replacement for perfumes based on alcoholic solvents, but they have not found wide commercial acceptance at this time. A problem with aqueous, ethanol-free or more generally polar solvent-free compositions is that they typically need to contain surfactants, and surfactants can create a feeling of greasiness when applied to the skin, as well as cause a sensation of skin tightening.

The provision of a perfume composition that is both polar solvent-free and/or surfactant-free would represent a significant step forward in perfumery, and in particular fine perfumery. In this regard, the compositions described in US 2014/0045949 could be potentially useful. However, as delivery vehicles for perfumes, the compositions described therein remain challenging.

A particular issue resides in the complexity of perfume compositions. In order to afford perfumers with the greatest latitude to create interesting olfactive impressions that will surprise and delight consumers, ideally they must have access to a full palette of perfumery ingredients. Typically perfumers will create mixtures containing a large number of perfume ingredients in the pursuit of desirable, multi-faceted and even polarizing perfume compositions.

Unfortunately, a problem with compositions based on droplets of perfume oil dispersed in an aqueous gel continuous phase is that many perfume ingredients may be chemically reactive with other elements of the compositions in which they are contained, and/or will readily migrate (or partition) into the surrounding aqueous continuous phase.

Loss of perfume from the dispersed phase is, of course, undesirable in its own right. However, migration of perfume ingredients can also lead to undesirable effects in the aqueous continuous phase, such as decrease in gel strength, which can result in creaming or sedimentation of the droplets; or loss of gel transparency due to syneresis. Either effect can lead to poor aesthetics, as well as causing difficulties in dispensing and applying the compositions onto a situs.

Furthermore, the applicant has found that the formation of droplets by a micro-fluidic or millifluidic process is sensitive to the nature of perfume ingredients. In the worst case, the use of incompatible perfume ingredients may make it impossible to form droplets, presumably due to the interference of those ingredients in the process of forming coacervates. More typically, however, the incompatibility of perfume ingredients in this process manifests itself in terms of phase demixing, phase whitening, unaesthetically looking wrinkles on the surface of the droplets, or undesirable colouration of the droplets.

There remains a need to provide perfume compositions, which can be presented in the form of substantially monodispersed, macroscopic droplets suspended in an aqueous medium, which droplets remain stably suspended during storage and through the useful life of the composition, thereby to provide an aesthetically pleasing visual appearance, and wherein the composition can be reliably dispensed and applied to a human or animal situs to provide a fragrance effect. More particularly, there remains a need to provide said compositions, which are free of alcoholic solvents, such as ethanol, or more generally free of polar solvents, and/or free of surfactants.

In accordance with the present invention there is provided a perfume composition, comprising more than 60 wt %, still more particularly more than 70 wt %, still more particularly more than 80 wt %, and more particularly still 90 wt % or more perfume ingredients, and wherein 25 wt % or less of said perfume ingredients are linear or branched alkyl alcohols and/or alkenyl alcohols; 10 wt % or less, preferably 5 wt % or less of the perfume ingredients are aldehydes; and 10 wt % or less, preferably 7.5 wt % or less of the perfume ingredients have a ClogP less than 2.1.

The applicant has found that perfume compositions as defined above are suitable to be presented in the form of macroscopic and monodispersed droplets suspended in an aqueous medium using a micro-fluidic or milli-fluidic process.

Accordingly, in another aspect of the present invention there is provided perfume composition, as defined above, presented in the form of a plurality of dispersed perfume-containing droplets, suspended in an aqueous dispersing medium, said perfume droplets being mono-dispersed and having a diameter of 200 micrometers to 4000 micrometers, wherein said droplets comprise more than 60 wt %, still more particularly more than 70 wt %, still more particularly more than 80 wt %, and more particularly still 90 wt % or more perfume ingredients, and wherein 25 wt % or less of said perfume ingredients are linear or branched alkyl alcohols and/or alkenyl alcohols; 10 wt % or less, preferably 5 wt % or less of the perfume ingredients are aldehydes; and 10 wt % or less, more particularly 7.5 wt % or less of the perfume ingredients have a ClogP less than 2.1.

In a particular embodiment of the invention, the perfume composition is free of polar solvents, and/or is free of surfactants.

As used herein, the term "free of a polar solvent" or "free of polar solvents" means that the perfume composition is free, or substantially free, of water-miscible or partially miscible solvents, and in particular alcoholic solvents, such as linear or branched alcoholic solvents, having 1 to 4 carbon atoms and at least one hydroxyl functional group. Said solvents include, ethanol, 1-propanol, 2-propanol, 1-butanol, 1,2-butanediol, 1,2-pentandiol 1,2-hexanediol, 1,2-heptanediol, 2-methyl-pentan-2,4-diol; glycol ethers, such as propylene glycol, dipropylene glycol, 1,3-propanediol Dowanol™ DPM, Dowanol™ TPM, Dowanol™ DPnP; methyl methoxy butanol, and mixture thereof. As used hereinabove, the term "substantially free" means less than 5% by weight based on the weight of the system.

As used herein, the term "surfactant-free" means that the perfume composition is free, or substantially free, of surfactants that are commonly used in alcohol-free perfume compositions, such as PEG 40 hydrogenated castor oil (Cremophor® RH 40 market by BASF), other types of the Cremophor® RH series, and PEG 400 (Lipoxol®  marketed by Sasol Olefins and Surfactants GmbH); C4-C18 alkyl ethoxylates with about 1-22 ethylene oxide units, Tergitol™ marked by The Dow Chemical Corporation, such as Tergitol™15-S-9 (the condensation product of C11-C15 linear secondary alcohol with 9 moles ethylene oxide), and Tergitol™ 24-L-6 NMW (the condensation product of C12-C14 primary alcohol with 6 moles ethylene oxide with a narrow molecular weight distribution); Neodol® marked by Shell Chemical Company, e.g., Neodol® 45-9 (the condensation product of C14-C15 linear alcohol with 9 moles of ethylene oxide), Neodol® 23-6.5 (the condensation product of C12-C13 linear alcohol with 6.5 moles of ethylene oxide), Neodol® 45-7 (the condensation product of C14-C15 linear alcohol with 7 moles of ethylene oxide), and Neodol® 45-4 (the condensation product of C14-C15 linear alcohol with 4 moles of ethylene oxide); Kyro® EOB (the condensation product of C13-C15 alcohol with 9 moles ethylene oxide), marketed by The Procter & Gamble Company; Cosmacol® N119 (the mixture of linear and mono branched C12-C13 with 9 moles of ethylene oxide), marketed by Sasol Olefins and Surfactants GmbH; Dehydol® series marketed by Cognis/BASF, preferably C8 to C18 (e.g. C10) with 2 to 14 moles of ethylene oxide, and mixtures thereof; Trideceth series, the condensation products of C13 alcohols and 2-21 moles of ethylene oxide, like Trideceth-9 and Trideceth-10, Dobanol® 91-8 marketed by Shell Chemical Co., and Genapol® UD-080 marketed by Clariant; mixed ethoxylates/propoxylates, such as Pluronic® surfactants, marketed by BASF, Eumulgin® L marketed by Cognis/BASF (e.g. PPG-1-PEG-9 lauryl glycol ether); condensation products of ethylene oxide (EO) with the product resulting from the reaction of propylene oxide and ethylene diamine. Examples of this type of non-ionic surfactants include certain of the commercially available Tetronic® compounds, marketed by BASF; alkyl dialkyl amine oxides, such as C10-C18 alkyl dimethyl amine oxides and C8-C12 alkoxy ethyl dihydroxy ethyl amine oxides; alkyl polyglycosides; alkanoyl glucose amides, glycol sorbitol ethers containing 3-30 EO units (including, for example, sorbitol esters with oleic, myristic, stearic, palmitic acid, and the like), also known under the tradename Tween, such as Tween 20, Tween 40, and Tween 60; alkyl polyglycosides including, for example, C8-C10 polyglycosides (e.g. Radia® Easysurf 6881, marketed by Oleon; Oramix™ CG110**, marketed by Seppic), C12-C16 alkyl polyglycosides (e.g. Plantaren® 1200 NP, marketed by Cognis/BASF), C8-C16 alkyl polyglycosides (e.g. Plantaren® 2000 marketed by Cognis/BASF), C5 Amyl xyloside (Radia® Easysurf 6505, marketed by Oleon) and mixture of C5 Amyl, C8 Capryl, C12 Lauryl xylosides (Radia Easysurf 6552, marketed by Oleon).

Perfume ingredients useful in perfume containing droplets are well known by a person skilled in the art and include those mentioned for example in S. Arctander, Perfume and Flavor Chemicals (Montclair, N.J., 1969), S. Arctander, Perfume and Flavor Materials of Natural Origin (Elizabeth, N.J., 1960) and in "Flavor and Fragrance Materials", 1991 (Allured Publishing Co. Wheaton, Ill. USA). The perfumes used in the context of the present invention may comprise terpenic esters, alkyl and alkenyl esters, cycloalkyl and cycloalkenyl esters, aromatic esters, aromatic alcohols, alkyl, alkenyl and aromatic ketones, alkyl, alkenyl and aromatic ketals and acetals, alkyl, alkenyl and aromatic ethers and oxides, alkyl, alkenyl and aromatic nitriles, azurone, cycloalkyl and cycloalkenyl alcohols, anethole, estragol, toscanol, diphenl oxide, hedione, ionones, irones, irisone, damascones, damascenone, galbanone, spirogalbanone, jasmones, javanol, radjanol, ebanol, macrocyclic musks, polycyclic musks, linear musks, alkyl and aromatic salicyclates, saturated and unsaturated polycyclic ketones, and the like.

Particular perfume ingredients include (1R,6S,8aS)-6-methoxy-1,4,4,6-tetramethyloctahydro-1H-5,8a-methanoazulene, (1S,2S,4S)-1,7,7-trimethylbicyclo[2.2.1]heptan-2-ol, (1s,4s)-1,3,3-trimethyl-2-oxabicyclo[2.2.2]octane, (1S,4S)-1,7,7-trimethylbicyclo[2.2.1]heptan-2-one, (2,2-dimethoxyethyl)benzene, (2E,6Z)-3,7-dimethylnona-2,6-dienenitrile, (2S,4S)-1,7,7-trimethylbicyclo[2.2.1]heptan-2-yl acetate, (3aR,6S,7aS)-3a,4,5,6,7,7a-hexahydro-1H-4,7-methanoinden-6-yl acetate, (3aR,6S,7aS)-3a,4,5,6,7,7a-hexahydro-1H-4,7-methanoinden-6-yl propionate, (3R,3aR,8R,8aS)-4,4,8-trimethyl-9-methylenedecahydro-3,8-methanoazulene, (4-isopropylcyclohexyl)methanol, (E)-1-(2,6,6-trimethylcyclohex-3-en-1-yl)but-2-en-1-one, (E)-2-ethyl-4-(2,2,3-trimethylcyclopent-3-en-1-yl)but-2-en-1-ol, (E)-3,7-dimethylnona-1,6-dien-3-ol, (E)-3,7-dimethylocta-2,6-dien-1-ol, (E)-3,7-dimethylocta-2,6-dien-1-yl acetate, (E)-3,7-dimethylocta-2,6-dienal, (E)-3-methyl-4-(2,6,6-trimethylcyclohex-2-en-1-yl)but-3-en-2-one, (E)-3-methyl-5-(2,2,3-trimethylcyclopent-3-en-1-yl)pent-4-en-2-ol, (E)-3-phenylprop-2-en-1-ol, (E)-4-(2,6,6-trimethylcyclohex-1-en-1-yl)but-3-en-2-one, (E)-4-(2,6,6-trimethylcyclohex-2-en-1-yl)but-3-en-2-one, (E)-4-methyldec-3-en-5-ol, (E)-methyl 2-((3-(4-(tert-butyl)phenyl)-2-methylprop-1-en-1-yl)amino)benzoate, (E)-oxacyclohexadec-12-en-2-one, (Z)-2-benzylideneheptanal, (Z)-3,4,5,6,6-pentamethylhept-3-en-2-one, (Z)-3,7-dimethylocta-2,6-dien-1-yl acetate, (Z)-hex-3-en-1-ol, (Z)-hex-3-en-1-yl 2-hydroxybenzoate, (Z)-hex-3-en-1-yl acetate, 1-((1S,8aS)-1,4,4,6-tetramethyl-2,3,3a,4,5,8-hexahydro-1H-5,8a-methanoazulen-7-yl)ethanone, 1-((1S,8aS)-1,4,4,6-tetramethyl-2,3,3a,4,5,8-hexahydro-1H-5,8a-methanoazulen-7-yl)ethanone, 1-(2,3,8,8-tetramethyl-1,2,3,4,5,6,7,8-octahydronaphthalen-2-yl)ethanone, 1-(2-naphtalenyl)-ethanone, hexamethyl-5,6,7,8-tetrahydronaphthalen-2-yl)ethanone, 1-(5,5-dimethylcyclohex-1-en-1-yl)pent-4-en-1-one, 1-(spiro[4.5]dec-7-en-7-yl)pent-4-en-1-one, 1,4-dioxacycloheptadecane-5,17-dione, 1,4-dioxacyclohexadecane-5,16-dione, 1-methoxy-4-methylbenzene, 1-methyl-4-(prop-1-en-2-yl)cyclohex-1-ene, 1-methyl-4-(propan-2-ylidene)cyclohex-1-ene, 1-phenylethyl acetate, 2-(1-(3,3-dimethylcyclohexyl)ethoxy)-2-methylpropyl cyclopropanecarboxylate, 2-(2-(4-methylcyclohex-3-en-1-yl)propyl)cyclopentanone, 2-(4-methylcyclohex-3-en-1-yl)propan-2-ol, 2-(4-methylcyclohex-3-en-1-yl)propan-2-yl acetate, 2-(6,6-dimethylbicyclo[3.1.1]hept-2-en-2-yl)ethyl acetate, 2-(secbutyl)cyclohexanone, 2-(tert-butyl)cyclohexyl acetate, 2,2,2-trichloro-1-phenylethyl acetate, 2,4-dimethylcyclohex-3-enecarbaldehyde, 2,6-dimethylhept-5-enal, 2,6-dimethylheptan-2-ol, 2,6-dimethyloctan-2-ol, 2-cyclohexylhepta-1,6-dien-3-one, 2-cyclohexylidene-2-phenylacetonitrile, 2-ethoxynaphthalene, 2-ethyl-3-hydroxy-4H-pyran-4-one, 2H-chromen-2-one, 2-methoxynaphthalene, 2-methyl-1-phenylpropan-2-yl acetate, 2-methyl-1-phenylpropan-2-yl butyrate, 2-methylundecanal, 2-phenoxyethanol, 2-phenoxyethyl isobutyrate, 2-phenylethanol, 3-((1R,2S,4R,6R)-5,5,6-trimethylbicyclo[2.2.1]heptan-2-yl)cyclohexanol, 3-(3-isopropylphenyl)butanal, 3-(4-(tert-butyl)phenyl)propanal, 3-(4-ethylphenyl)-2,2-dimethylpropanal, 3-(4-isopropylphenyl)-2-methylpropanal, 3-(benzo[d][1,3]dioxo1-5-yl)-2-methylpropanal, 3,5,5-trimethylhexyl acetate, 3,7-dimethyloct-6-en-1-ol, 3,7-dimethyloct-6-en-1-yl acetate, 3,7-dimethyloct-6-enenitrile, 3,7-dimethylocta-1,6-dien-3-yl acetate, 3,7-dimethyloctan-1-ol, 3,7-dimethyloctan-3-ol, 3a,6,6,9a-tetramethyldodecahydronaphtho[2,1-b]furan, 3-methoxy-3-methylbutan-1-ol, 3-methyl-5-(2,2,3-trimethylcyclopent-3-en-1-yl)pentan-2-ol, 3-methylbut-2-en-1-yl acetate, 3-pentyltetrahydro-2H-pyran-4-yl acetate, 4-(4-hydroxy-4-methylpentyl)cyclohex-3-enecarbaldehyde, 4-(4-hydroxyphenyl)butan-2-one, 4-(tert-butyl)cyclohexyl acetate, 4,6,6,7,8,8-hexamethyl-1,3,4,6,7,8-hexahydrocyclopenta[g]isochromene, 4-allyl-2-methoxyphenol, 4-hydroxy-3-methoxybenzaldehyde, 4-methoxybenzaldehyde, 4-methyl-2-(2-methylprop-1-en-1-yl)tetrahydro-2H-pyran, 4-phenylbutan-2-one, 5-heptyldihydrofuran-2(3H)-one, 5-hexyldihydrofuran-2(3H)-one, 5-pentyldihydrofuran-2(3H)-one, 6,6-dimethyl-2-methylenebicyclo[3.1.1]heptane, 7-hydroxy-3,7-dimethyloctanal, allyl 2-(isopentyloxy)acetate, allyl 3-cyclohexylpropanoate, allyl heptanoate, allyl hexanoate, benzo[d][1,3]dioxole-5-carbaldehyde, benzyl 2-hydroxybenzoate, benzyl benzoate, benzyl acetate, benzyl cinnamate, decanal, dodecanal, ethyl 2-(2-methyl-1,3-dioxolan-2-yl)acetate, ethyl 2-methylbutanoate, ethyl 2-methylpentanoate, ethyl 3-oxobutanoate, hexanal, hexyl 2-hydroxybenzoate, hexyl acetate, isopentyl acetate, methyl 2-(3-oxo-2-pentylcyclopentyl)acetate, methyl 2-(3-oxo-2-pentylcyclopentyl)acetate, methyl 2,4-dihydroxy-3,6-dimethylbenzoate, methyl 2-aminobenzoate, methyl benzoate, octanal, oxacyclohexadecan-2-one, oxydibenzene, pentyl 2-hydroxybenzoate, phenethyl acetate, propane-1,2,3-triyl triacetate, tetrahydro-4-methyl-2-(2-methylpropyl)-2H-pyran-4-ol, Particular linear or branched alkyl and/or alkenyl alcohols include terpenic alcohols, such as decan-1-ol, dodecan-1-ol, tridecan-1-ol, hexan-1-ol, octan-1-ol, nonan-1-ol, 3,7-dimethyloct-6-en-1-ol, 2,6-dimethyloctan-2-ol, 3,7-dimethyloct-6-en-1-ol, 2,6-dimethyloct-7-en-2-ol, 2,6-dimethylheptan-2-ol, (E)-3,7-dimethylnona-1,6-dien-3-ol, (2E,6Z)-3,7,11-trimethyldodeca-2,6,10-trien-1-ol, (E)-3,7-dimethylocta-2,6-dien-1-ol, (E)-hex-2-en-1-ol, (Z)-hex-3-en-1-ol, 3,5,5-trimethylhexan-1-ol, 3,7-dimethylocta-1,6-dien-3-ol, 3,7-dimethylocta-1,6-dien-3-ol, 2,6-dimethyloctan-2-ol, 2-methylbutan-1-ol, (Z)-3,7,11-trimethyldodeca-1,6,10-trien-3-ol, (2E,6Z)-nona-2,6-dien-1-ol, (2E,6Z)-nona-2,6-dien-1-ol, 6,8-dimethylnonan-2-ol, (Z)-non-6-en-1-ol, 3,7-dimethyloctan-1-ol, 3-methylpentan-1-ol, 3-methyl-but-2-en-1-ol, 3,7-dimethyloctan-3-ol. Such alcohols have typically 8 carbon atoms an more, for example 10 carbon atoms and more.

Particular aldehydes include 2,6,10-trimethylundec-9-enal, 1-methyl-4-(4-methylpentyl)cyclohex-3-enecarbaldehyde, decanal, 2-methyldecanal, undec-10-enal, undecanal, dodecanal, 2-methylundecanal, hexanal, heptanal, octanal, 3,5,5-trimethylhexanal, nonanal, (E)-non-2-enal, (E)-undec-9-enal, heptanal, (E)-dodec-2-enal, hexanal, (Z)-2-benzylideneheptanal, 4-methoxybenzaldehyde, benzaldehyde, 3-(4-(tert-butyl)phenyl)propanal, 6-methoxy-2,6-dimethyloctanal, 2-methyl-4-(2,6,6-trimethylcyclohex-2-en-1-yl)butanal, cinnamaldehyde, (E)-3,7-dimethylocta-2,6-dienal, (E)-3,7-dimethylocta-2,6-dienal, 3,7-dimethyloct-6-enal, 2-((3,7-dimethyloct-6-en-1-yl)oxy)acetaldehyde, 4-isopropylbenzaldehyde, 2,4-dimethylcyclohex-3-enecarbaldehyde, 3-(4-isopropylphenyl)-2-methylpropanal, 8,8-dimethyl-1,2,3,4,5,6,7,8-octahydronaphthalene-2-carbaldehyde, 8,8-dimethyl-1,2,3,4,5,6,7,8-octahydronaphthalene-2-carbaldehyde, 4-(4-hydroxy-4-methylpentyl)cyclohex-3-enecarbaldehyde, (2E,4E)-deca-2,4-dienal, (E)-dec-2-enal, (E)-dec-4-enal, 9-decenal, (Z)-3,7,11-trimethyldodeca-6,10-dienal, (E)-dodec-2-enal, (E)-4-((3aS,7aS)-hexahydro-1H-4,7-methanoinden-5(6H)-ylidene)butanal, 3-ethoxy-4-hydroxybenzaldehyde, 3-(4-methoxyphenyl)-2-methylpropanal, 3-(4-ethylphenyl)-2,2-dimethylpropanal, 3-(3-isopropylphenyl)butanal, benzo[d][1,3]dioxole-5-carbaldehyde, (E)-hex-2-enal, (E)-2-benzylideneoctanal, 2-phenylpropanal, 7-hydroxy-3,7-dimethyloctanal, 2,4,6-trimethylcyclohex-3-enecarbaldehyde, 3-(4-(tert-butyl)phenyl)-2-methylpropanal, bicyclo[2.2.2]oct-5-ene-2-carboxaldehyde, 3-methyl-5-phenylpentanal, 6-methoxy-2,6-dimethylheptanal, 2,6-dimethylhept-5-enal, (Z)-2-methyl-3-phenylacrylaldehyde, 4-(4-methylpent-3-en-1-yl)cyclohex-3-enecarbaldehyde, (2E,6Z)-nona-2,6-dienal, (Z)-non-6-enal, (E)-2,6,10-trimethylundeca-5,9-dienal, 2-phenoxyacetaldehyde, 2-phenylacetaldehyde, 3-phenylpropanal, 3-(6,6-dimethylbicyclo[3.1.1]hept-2-en-2-yl)propanal, 1-methyl-4-(4-methylpent-3-en-1-yl)cyclohex-3-enecarbaldehyde, 2,6,6-trimethylcyclohexa-1,3-dienecarbaldehyde, (3aR,4R,6S,7R,7aR)-6-methoxyoctahydro-1H-4,7-methanoindene-1-carbaldehyde, 3-(4-isobutylphenyl)-2-methylpropanal, 2-(p-tolyl)acetaldehyde, 3,7-dimethyloctanal, (E)-undec-2-enal, 2,4-dimethylcyclohex-3-enecarbaldehyde, 3-phenylbutanal, 3-(benzo[d][1,3]dioxo1-5-yl)-2-methylpropanal, 4-hydroxy-3-methoxybenzaldehyde, (E)-9-hydroxy-5,9-dimethyldec-4-enal, 3-(4-isobutyl-2-methylphenyl)-propanal, 9-hydroxy-5,9-dimethyldecanal.

Particular perfume ingredients having ClogP values less than 2.1 include 1-(pyrazin-2-yl)ethanone, 3-hydroxy-2-methyl-4H-pyran-4-one, 4-ethyl-5-methylthiazol-2-ol, methyl-2-pyrazine, 3-hydroxy-4,5-dimethylfuran-2(5H)-one, ethyl 3-oxobutanoate, 2-hydroxy-3-methylcyclopent-2-enone, 3-methoxy-3-methylbutan-1-ol, 2-ethyl-3-hydroxy-4H-pyran-4-one, 1-(thiazol-2-yl)ethanone, ethyl acetate, 2-methyl-4-oxo-4H-pyran-3-yl isobutyrate, 5-propyldihydrofuran-2(3H)-one, (4-methoxyphenyl)methanol, phenylmethanol, diethyl malonate, 2-methoxy-3-methylpyrazine, (2-benzyl-1,3-dioxolan-4-yl)methanol, ethyl 2-(2-methyl-1,3-dioxolan-2-yl)acetate, triethyl 2-hydroxypropane-1,2,3-tricarboxylate, octahydro-2H-chromen-2-one, 2-phenoxyethanol, 2-phenoxyacetaldehyde, 2-methylbutan-1-ol, 4-(4-hydroxyphenyl)butan-2-one, ethyl propanoate, 4-hydroxy-3-methoxybenzaldehyde, 5-butyldihydrofuran-2(3H)-one, 2-methoxyphenol, 6-propyltetrahydro-2H-pyran-2-one, 2-phenylethanol, tetrahydro-4-methyl-2-(2-methylpropyl)-2H-pyran-4-ol, (Z)-hex-3-en-1-ol, 4,4a,5,9b-tetrahydroindeno[1,2-d][1,3]dioxine, 2H-chromen-2-one, 2-phenylacetic acid, benzaldehyde, benzyl formate, 7-hydroxy-3,7-dimethyloctanal, ethyl 2-methylpropanoate, methyl 2-methylbutanoate, 4-methoxy-2-methylbutane-2-thiol, (2,2-dimethoxyethyl)benzene, (E)-hex-2-enal, acetophenone, (3aR,4R,6S,7R,7aR)-6-methoxyoctahydro-1H-4,7- methanoindene-1-carbaldehyde, (E)-hex-2-en-1-ol, 2-ethyl-4-hydroxy-5-methylfuran-3(2H)-one, (E)-3-phenylprop-2-en-1-ol, 2-ethoxy-4-(methoxymethyl)phenol, 2-(2-hydroxypropan-2-yl)-5-methylcyclohexanol, ethyl 2-(2,4-dimethyl-1,3-dioxolan-2-yl)acetate, 8-methyl-1-oxaspiro[4.5]decan-2-one, 3-phenylpropan-1-ol, 4-formyl-2-methoxyphenyl isobutyrate, (E)-2-methylpent-2-enoic acid, benzo[d][1,3]dioxole-5-carbaldehyde, butyl acetate, ethyl butyrate, 4-methoxybenzaldehyde, 2-(o-tolyl)ethanol, 2-phenylacetaldehyde, ethyl 6-acetoxyhexanoate, 1-(4-methoxyphenyl)ethanone, 7-methyl-2H-benzo[b][1,4]dioxepin-3(4H)-one, 4-(4-methoxyphenyl)butan-2-one, 3-ethoxy-4-hydroxybenzaldehyde, methyl 2-phenylacetate, 6-methylhept-5-en-2-one, 2-methoxy-4-methylphenol, 2-(5-methyl-5-vinyltetrahydrofuran-2-yl)propan-2-ol, 5-pentyldihydrofuran-2(3H)-one, phenethyl formate, 4-(1-3-benzodioxol-5-yl)-2-butanone, 6-methoxy-2,6-dimethylheptanal, 3-phenylpropanal, 4-methoxybenzyl acetate, hexan-1-ol, 3-methylbut-2-en-1-yl acetate, 4-phenylbutan-2-one, hexanal, (Z)-hex-3-en-1-yl formate, (Z)-6-(pent-2-en-1-yl)tetrahydro-2H-pyran-2-one, (E)-6-(pent-3-en-1-yl)tetrahydro-2H-pyran-2-one, heptan-2-one, 8,8-dimethoxy-2,6-dimethyloctan-2-ol, (methoxymethyl)benzene, benzyl acetate, (1,1-dimethoxypropan-2-yl)benzene, p-cresol, p-tolyl acetate, 4-methyl-benzaldehyde, 2-methyl-5-(prop-1-en-2-yl)cyclohex-2-enone, 7-methoxy-3,7-dimethyloctan-2-ol, 2-methyl-1-phenylpropan-2-ol, cinnamaldehyde, (2-methoxyethyl)benzene, 3-methoxy-5-methylphenol, ethyl 2-methylbutanoate, 1-(p-tolyl)ethanone, 2-phenylpropanal.

The perfume-containing droplets, in addition to the perfume ingredients, may contain other ingredients such as colorants, stabilizers, chelating agents, preservatives, emollients, modifiers selected from agents for modifying texture, viscosity, pH, osmotic force or refractive index, and mixtures thereof.

Among the preservatives, can be mentioned phenoxyethanol, pentylene glycol and EDTA. According to one embodiment, the dispersions according to the invention comprise at least one preservative, and preferably a mixture of several preservatives.

The perfume-containing droplets may also contain, in addition to the perfume ingredients, a fraction of a first coacervate precursor, which has not completely reacted or interacted with a second coacervate precursor polymer and therefore is not confined to the coacervate layer coating the droplets.

The perfume-containing droplets, in addition to the perfume ingredients, may contain an oil selected from silicone oils, polydimethylsiloxane and copolymer of dimethylsiloxane and alkyl oxides, mineral oils, vegetable oils, linear of branched fatty acid esters and/or fatty alcohol esters, typically $C_1$ to $C_{20}$ esters, an oils compatible with the esters such as apolar solvents.

Particularly preferred oils are selected from polydimethylsiloxanes (PDMS), poly(ethyle oxide-b-dimethylsiloxane) and isononyl isononaoate.

As used herein, the term "perfume composition" excludes the coacervate coating the perfume-containing droplets.

The term "system" used hereinafter, refers to the perfume composition, in the form of a plurality of perfume-containing droplets, together with the suspending medium in which these droplets are dispersed, and includes the coacervate that coats the perfume-containing droplets.

The total amount of perfume ingredients expressed as a percentage by weight (wt %) of the system may be between 1 to 20 wt %, more particularly between 3 and 15% wt %, and still more preferably between 5 and 10 wt %.

As used herein, the diameter of the droplets is expressed as the arithmetic mean diameter of the droplets and is between 200 µm and 4000 µm, and preferably between 250 µm and 2000 µm, and more preferably between 500 µm and 1500 µm.

In the context of the present invention, the term "macroscopic" is used in relation to the droplets means that the droplets are visible to the human eye such that they provide a particular aesthetic effect reminiscent of substantially spherical particles. For the avoidance of doubt, droplets having a diameter referred to above are "macroscopic" for the purpose of the present invention.

The term "mono-dispersed" as it is used in relation to the droplets, means that the droplets have a substantially uniform size distribution. In a particular embodiment of the present invention, the droplets are mono-dispersed when they possess a coefficient of variation (Cv) about their diameter that is about 10% or less, more particularly below 5%, and still more particularly below 3%.

The diameter $\overline{D}$ of the droplets may be measured by analysis of a photograph of a batch consisting of N droplets, with image processing software (Image J). Typically, according to this method, the diameter is measured in pixels, before being converted to µm, as a function of the size of the vessel containing the droplets of the dispersion.

Preferably, the value of N is selected such that it is greater than or equal to 30, so that this analysis reflects, in a statistically significant manner, the distribution of diameters of the droplets.

The diameter Di of each droplet is measured, then the diameter $\overline{D}$ is found by calculating the arithmetic mean of these values:

$$\overline{D} = \frac{1}{N}\sum_{i=1}^{N} D_i$$

Starting from these values $D_i$, we may also obtain the standard deviation σ of the diameters of the droplets of the dispersion:

$$\sigma = \sqrt{\frac{\sum_{i=1}^{N}(D_i - \overline{D})^2}{N}}$$

The standard deviation σ of a dispersion reflects the distribution of the diameters $D_i$ of the droplets of the dispersion around the diameter $\overline{D}$.

Knowing the diameter $\overline{D}$ and the standard deviation σ of a dispersion, it can be determined that 95.4% of the population of droplets occurs in the range of diameters [$\overline{D}$−2σ; $\overline{D}$+2σ] and that 68.2% of the population occurs in the range [$\overline{D}$−σ;$\overline{D}$+σ].

To characterize the mono-dispersity of the droplets the coefficient of variation may be calculated:

$$C_v = \frac{\sigma}{\overline{D}}$$

This parameter reflects the distribution of the diameters of the droplets as a function of their diameter.

Alternatively, the mono-dispersity may be demonstrated by putting a sample of suspended droplets in a bottle with constant circular cross-section. Gentle stirring can be provided by rotation by a quarter turn in half a second about the axis of symmetry passing through the bottle, followed by resting for half a second, before repeating the operation in the opposite direction, four more times.

The droplets self-organize in a crystalline form when they are mono-dispersed. Thus, they present stacking following a pattern that repeats in the three dimensions. It is then possible to observe regular stacking, which indicates good mono-dispersity, and irregular stacking reflects poly-dispersity of the droplets.

The perfume-containing droplets are dispersed in a suitable aqueous continuous phase, which is in the form of a gel.

The aqueous continuous phase comprises at least one crosslinked polymer or at least one crosslinked copolymer, said crosslinked polymer or crosslinked copolymer comprising at least one unit derived from the polymerization of one of the following monomers: acrylic or methacrylic acid, alkyl acrylate or methacrylate comprising from 1 to 30 carbon atoms, or salts thereof.

The continuous phase may also comprise a mixture of crosslinked polymers or a mixture of crosslinked copolymers or a mixture of crosslinked polymer(s) and crosslinked copolymer(s).

According to the invention, the term "unit derived from the polymerization of a monomer" signifies that the polymer or copolymer is a polymer or copolymer obtained by polymerization or copolymerization of said monomer.

According to one embodiment, the crosslinked polymer or crosslinked copolymer is a crosslinked polyacrylate.

In a particular embodiment, the crosslinked copolymers and polymers are anionic.

According to one embodiment, the copolymer is a copolymer of unsaturated carboxylic acid and of unsaturated $C_{1-30}$, preferably $C_1$-$C_4$, alkyl carboxylate. Such a copolymer comprises at least one hydrophilic unit of the unsaturated olefinic carboxylic acid type and at least one hydrophobic unit of the type of $(C_1$-$C_{30})$ alkyl ester of unsaturated carboxylic acid.

Preferably, these copolymers are selected from those whose hydrophilic unit of the unsaturated olefinic carboxylic acid type corresponds to the monomer of the following formula

in which: $R_1$ denotes H or $CH_3$ or $C_2H_5$, i.e. acrylic acid, methacrylic acid or ethacrylic acid units, and in which the hydrophobic unit of the type of $(C_1$-$C_{30})$ alkyl ester of unsaturated carboxylic acid corresponds to the monomer of the following formula (II):

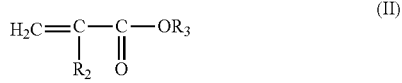

in which: $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_1$-$C_{30}$, and preferably $C_1$-$C_4$, alkyl radical.

Among copolymers of this type, more particularly those formed from a mixture of monomers will be used comprising:

(i) acrylic acid, (ii) an ester of formula (II) described above, in which $R_2$ denotes H or $CH_3$, $R_3$ denoting an alkyl radical having from 1 to 4 carbon atoms, and (iii) a crosslinking agent, which is an unsaturated copolymerizable polyethylene monomer, such as diallyl phthalate, trimethylolpropane tri(meth)acrylate, diallyl itaconate, diallyl fumarate, diallyl maleate, zinc (meth)acrylate, allyl (meth)acrylate, divinylbenzene, (poly)ethylene glycol dimethacrylate, methylene-bis-acrylamide, and castor oil.

According to one embodiment, the polymer or the copolymer is a polymer or copolymer of acrylic acid and/or of methacrylic acid, and/or of alkyl acrylate comprising from 1 to 30 carbon atoms, preferably from 1 to 4 carbon atoms, and/or of alkyl methacrylate comprising from 1 to 30 carbon atoms, preferably from 1 to 4 carbon atoms.

According to one embodiment, the crosslinked copolymer is a crosslinked copolymer of methacrylic acid and of alkyl acrylate comprising from 1 to 4 carbon atoms, preferably 2 carbon atoms.

In the context of the present invention, and unless stated otherwise, "crosslinked copolymer of methacrylic acid and of alkyl acrylate comprising from 1 to 4 carbon atoms" means a crosslinked copolymer resulting from the polymerization of a monomer of methacrylic acid and a monomer of alkyl acrylate comprising from 1 to 4 carbon atoms.

Preferably, in this copolymer, methacrylic acid represents from 20 to 80 wt %, preferably from 35 to 65 wt % of the total weight of the copolymer.

Preferably, in this copolymer, alkyl acrylate represents from 15 to 80 wt %, preferably from 35 to 65 wt % of the total weight of the copolymer.

In particular, the alkyl acrylate is selected from alkyl methacrylate, ethyl acrylate and butyl acrylate.

According to one embodiment, the crosslinked polymer or the crosslinked copolymer according to the invention, present in the aqueous continuous phase, is selected from the group consisting of the following polymers or copolymers: acrylates copolymer, acrylates crosspolymer-4, acrylates crosspolymer-3, polyacrylate-2 crosspolymer and polyacrylate-14 (INCI names).

Among the aforementioned polymers, the products sold by the company LUBRIZOL under the trade names Fixate Superhold (INCI name=Polyacrylate-2 Crosspolymer), Fixate Freestyle Polymer (INCI name=Acrylates crosspolymer-3), Carbopol® Aqua SF1 (INCI name=Acrylates copolymer) and Carbopol® Aqua SF2 (INCI name=Acrylates crosspolymer-4) are quite particularly preferred according to the present invention.

Preferably, the crosslinked polymer or the crosslinked copolymer is selected from Carbopol® Aqua SF1 (INCI name=Acrylates copolymer) and Carbopol® Aqua SF2 (INCI name=Acrylates crosspolymer-4). In particular, it is Carbopol® Aqua SF2 (INCI name=Acrylates crosspolymer-4).

According to one embodiment, the crosslinked copolymer is selected from the crosslinked copolymers of acrylic or methacrylic acid and of alkyl acrylates comprising from 1 to 4 carbon atoms.

The crosslinked polymer or crosslinked copolymer may be present in an amount of 0.1 to 10 wt %, preferably from 0.5 to 8 wt %, and preferably from 1 to 3 wt % based on the total weight of the system.

In accordance with the present invention, the perfume-containing droplets are coated with layer of coacervate. The coacervate layer is applied to the droplets in order to retain perfume ingredients within the droplets, and to prevent the droplets from coalescing.

The process of coacervation is well known in the art. It proceeds by bringing into contact first and second coacervate precursor polymers. The first coacervate precursor polymer may be cationic, or is capable of forming cations under conditions of the coacervation process, whereas, the second coacervation precursor polymer may be anionic, or is capable of forming anions under the conditions of the coacervation process. The oppositely charged polymers are caused to interact to form the coacervate layer in response to a change of conditions within the mixture of the polymers, for example a change in temperature, pH, concentration of the polymers, or the like. Ionic bonds bind the oppositely charged polymers together in the layer to form a layer around the droplets, this layer being sufficiently rigid to prevent droplet coalescence.

One of the coacervate precursor polymers is a polymer possessing anionic charges, or which can be caused to form anionic charges.

As examples of chemical functions of anionic type, we may mention the carboxylic acid functions —COOH, optionally present in the form of carboxylate anion —COO—.

As an example of such a polymer we may mention any polymer formed by the polymerization of monomers, at least a proportion of which bear carboxylic acid functions. Such monomers are for example acrylic acid, maleic acid, or any ethylenically unsaturated monomer comprising at least one carboxylic acid functional group.

Examples of such polymers include the copolymers of acrylic acid or of maleic acid and of other monomers, such as acrylamide, alkyl acrylates, C5-C8 alkyl acrylates, C10-C30 alkyl acrylates, C12-C22 alkyl methacrylates, methoxypolyethylene glycol methacrylates, hydroxy ester acrylates, acrylates crosspolymers.

Preferred polymers bearing anions, or capable of forming anions, are carbomers. Other useful polymers that can be employed are crosslinked acrylates/C10-30 alkyl acrylate copolymer (INCI name: acrylates/C10-30 alkyl acrylate Crosspolymer).

In a particular embodiment, it is possible to employ both a carbomer and a crosslinked acrylate/C10-30 alkyl acrylate copolymer.

The term "carbomer" is used to describe a homopolymer, optionally crosslinked, resulting from the polymerization of acrylic acid. It is therefore a poly(acrylic acid), optionally crosslinked.

Among the carbomers of the invention, we may mention those marketed under the name Tego Carbomer 340FD from Evonik or Carbopol® 981 and the carbopol Ultrez 10 from Lubrizol.

According to one embodiment, "carbomer" or "Carbopol®" means a polymer of acrylic acid of high molecular weight crosslinked with allyl sucrose or allyl ethers of pentaerythritol (Handbook of Pharmaceutical Excipients, 5th Edition, p. 111). For example, it is carbomer 910, carbomer 934, carbomer 934P, carbomer 940, carbomer 941, carbomer 71G, carbomer 980, carbomer 971P or carbomer 974P. According to one embodiment, the viscosity of said carbomer is between 4000 and 60 000 cP at 0.5% w/w.

The carbomers have other names, such as polyacrylic acids, carboxyvinyl polymers or carboxy polyethylenes.

The carbomer may be present in amounts of 0.05 to 5 wt %, preferably from 0.1 to 2 wt %, and more preferably from 0.15 to 0.5 wt % of carbomer relative to the total weight of the system.

Another of the coacervate precursor polymers is a cationic polymer, or a polymer that can form cations under conditions of the coacervation process.

These polymers may be polymers possessing primary, secondary and tertiary amine functions, optionally present in the form of ammonium cations.

As an example of polymer of cationic type, we may mention any polymer formed by the polymerization of monomers, at least a proportion of which bear chemical functions of cationic type, such as primary, secondary or tertiary amine functions.

Such monomers are for example aziridine, or any ethylenically unsaturated monomer comprising at least one primary, secondary or tertiary amine function.

Among the particular examples of these polymers we may mention amodimethicone, derived from a silicone polymer (polydimethylsiloxane, also called dimethicone), modified with primary amine and secondary amine functions:

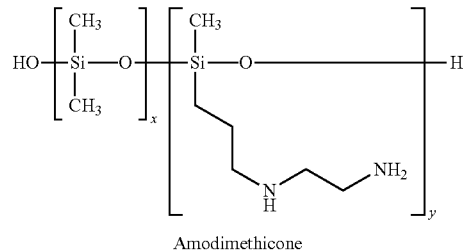

Amodimethicone

We may also mention derivatives of amodimethicone, for example copolymers of amodimethicone, aminopropyl dimethicone, and more generally silicone polymers bearing amine functions.

We may mention the copolymer of bis-isobutyl PEG-14/amodimethicone, bis(C13-15 alkoxy) PG-amodimethicone, bis-cetearyl amodimethicone and bis-hydroxy/methoxy amodimethicone.

We may also mention the polymers of the polysaccharide type comprising amine functions, such as chitosan or the derivatives of guar gum (hydroxypropyltrimonium guar chloride).

We may also mention the polymers of the polypeptide type comprising amine functions, such as polylysine.

We may also mention the polymers of the polyethyleneimine type comprising amine functions, such as linear or branched polyethyleneimine.

The amount of cationic polymer present may be between 0.05 to 5 wt %, preferably from 0.1 to 2 wt %, and more preferably from 0.15 to 0.5 wt % based on the total weight of the fragrance-containing droplets.

There are a variety of ways of presenting perfume compositions in the form of perfume-containing droplets suspended in an aqueous continuous phase. However, in accordance with the present invention, in order to produce macroscopic perfume-containing droplets that are monodispersed, a process of micro-fluidization or milli-fluidization is employed Accordingly, in another aspect of the present invention there is provided a method of preparing a perfume composition in the form of perfume-containing droplets as hereinabove defined, said method comprising the steps of I) passing a mixture of said perfume composition and a first coacervate precursor polymer through a first conduit; and II) forming perfume-containing droplets of said perfume composition at the outlet of said first conduit, which outlet opens into a second fluid comprising an aqueous continuous phase, and a hydrophilic coacervate precursor polymer that is interactive with a second coacervate precursor polymer to form coacervate coatings around said droplets.

In a particular embodiment of the invention, the first conduit is coaxially arranged inside a second conduit. The first conduit contains a stream of perfume composition and a first coacervate precursor polymer, which forms into droplets at the exit of said first conduit. The outlet of the first conduit opens the second conduit, which contains a stream of said second fluid comprising the aqueous continuous phase, and a second coacervate precursor polymer that is interactive with the first coacervate precursor polymer to form coacervate coatings around said droplets In a particular embodiment of the present invention, said second conduit opens downstream into a receptacle for receiving the droplets of perfume composition dispersed in the aqueous continuous phase.

In a particular embodiment of the present invention, the first coacervate precursor polymer contained in the first conduit is preferably a cationic polymer, whereas, a second coacervate precursor polymer, preferably an anionic polymer, is contained in the second conduit containing the stream of aqueous continuous phase. In such an arrangement, coacervation to form the layer of coacervate around the droplets can take place as the droplets exiting the outlet of the first conduit enter the stream of fluid in the second conduit, enabling the first and second coacervate precursor polymers to interact at the interface of the droplets and the aqueous continuous phase.

Typically, the flow rate of the fluid in the second conduit is between 6 and 100 ml/hour and the internal fluid is between 4 and 20 ml/hour.

In a particular embodiment of the present invention, a further coaxial stream, intermediate between said first and second conduit may be employed. This stream comprises an oil which is miscible with the perfume-containing stream in the first conduit. The intermediate stream consists, for example, at least one oil selected from silicone oils, mineral oils, vegetable oils, linear of branched fatty acid esters and/or fatty alcohol esters, typically $C_1$ to $C_{20}$ esters, an oil compatible with the esters such as apolar solvents. This oil promotes the controlled formation of the coacervate by promoting the migration of the first coacervate precursor to the interface between the droplets and the external phase. This intermediate stream may flow at a rate that is between 2 and 10 ml/hour.

In a particular embodiment, said additional coaxial stream may comprise a base, preferably an inorganic base, and most preferably sodium hydroxide. This base controls the formation of the gel in the continuous phase by neutralizing the carbomer in a controlled way.

A micro-fluidic or milli-fluidic process is more fully described in US2014/0045949, which is hereby incorporated by reference.

As stated hereinabove, the applicant surprisingly found that the coacervation process is sensitive to the nature of the perfume ingredients used in the droplets. Applicant found that adherence to the rules related to the perfume mixture, set forth hereinabove, enabled macroscopic, mono-dispersed droplets to be formed with the desired aesthetics.

Accordingly, the invention provides in another of its aspects, the use of a perfume composition as hereinabove defined to provide a perfume composition in the form of a plurality of dispersed perfume-containing droplets, suspended in an aqueous dispersing medium, said perfume droplets being mono-dispersed and having a diameter of 200 micrometers to 4000 micrometers, wherein said droplets comprise more than 60 wt %, still more particularly more than 70 wt %, still more particularly more than 80 wt %, and more particularly still 90 wt % or more perfume ingredients, and wherein 25 wt % or less of said perfume ingredients are linear or branched alkyl alcohols and/or alkenyl alcohols; 10 wt % or less, preferably 5 wt or less of the perfume ingredients are aldehydes; and 10 wt % or less, preferably 7.5 wt % or less of the perfume ingredients have a ClogP less than 2.1.

In a particular embodiment the perfume composition is free of alcoholic or polar solvents, and/or is free of surfactants.

The layer of the coacervate formed around perfume-containing droplets in a manner described hereinabove, is very thin, and in a particular embodiment may have a thickness that is about 1% of the diameter of the droplets. Thus, the thickness of the layer may be less than 1 µm, and more particularly less than 1000 nm, still more particularly from about 1 to 500 nm, still more particularly less than 100 nm, still more particularly less than 50 nm, and more particularly still less than 10 nm.

The thickness of the layer surrounding the droplets of may be measured by the method of small-angle neutron scattering (Small-Angle X-ray Scattering), as employed in Sato et al. J. Chem. Phys. 111, 1393-1401 (2007), incorporated herein by reference. In order to carry out this measurement, the droplets are produced using deuterated water, and then are washed with a deuterated oil, for example a deuterated hydrocarbon oil, such as octane, dodecane or hexadecane.

After washing, the droplets are then transferred to the neutron cell in order to determine the spectrum 1(q); q being the wave vector.

Starting from this spectrum, the conventional analytical treatments (REF) are applied in order to determine the thickness of the hydrogenated (not deuterated) layer.

It will be understood that reference hereinabove to the diameter of the droplets, is intended to refer to the diameter of the droplet including the coavervate layer around the droplet.

As is clear from the foregoing, it is an aim of the present invention to provide a perfume composition, which may be presented in the form of a plurality of macroscopic and mono-dispersed droplets. Furthermore, it should be possible to stably disperse the droplets in an aqueous continuous phase, which is in the form of a gel to form the system, which can be filled into suitable containers, from which it can be dispensed and applied to a human or animal situs, such as skin or hair to provide a perfuming effect.

The gel should have a viscosity that is compatible with ease of handling and operations associated with the preparation, transportation and storage of the system. The viscosity of the gel must also be compatible with requirement that the droplets must remain suspended in the gel in an aesthetically acceptable manner during manufacture, transportation, storage and during use by a consumer. The viscosity of the gel must further be compatible with the requirement that is must be dispensible in the form of a spray or in the form of a serum, even after prolonged storage under elevated temperature conditions, such as those prevailing in the stability testing of perfumery products (e.g. 3 months at 40 to 50° C.).

The viscosity may be measured at room temperature, for example T=25° C.±2° C. and at ambient pressure, for example 1013 mbar, by the following method.

A viscosimeter of the Brookfield type is used, typically a Brookfield RVDV-E digital viscosimeter (spring torque of 7187.0 dyne-cm), which is a rotary viscosimeter with imposed speed equipped with a spindle. A speed is imposed on the rotating spindle and measurement of the torque exerted on the spindle allows the viscosity to be determined, knowing the parameters of geometry/shape of the spindle used.

For example a spindle of size No. 04 is used (Brookfield reference: RV4). The shear rate corresponding to the measurement of the viscosity is defined by the spindle used and the rotary speed of the latter.

The viscosity is measured over 1 minute at room temperature (T=25° C.±2° C.). About 150 g of solution is put in a 250-ml beaker, having a diameter of about 7 cm, in such a way that the height of the volume occupied by the 150 g of solution is sufficient to reach the gauge mark on the spindle. Then the viscosimeter is started at a speed of 10 rev/min and we wait until the value displayed on the screen is stable. This measurement gives the viscosity of the fluid tested, as mentioned in the context of the present invention.

A suitable viscosity for the gel, as measured under above conditions (spindle size No 04 at 10 rev/min) is preferably in the range from 400 mPa·s to 20 000 mPa·s, preferably from 800 mPa·s to 15 000 mPa·s.

Having regard to the foregoing, the perfume ingredients employed in the perfume compositions of the present invention should not adversely affect the viscostability of the gels in which they are suspended to form the system.

However, despite taking all precautions related to the design of the perfume composition in order to prevent or limit migration of perfume into the gel, it always remains a possibility that small amounts of certain perfume ingredients could migrate. Furthermore, some perfumery ingredients, such as short chain esters, which are prone to hydrolysis, and other perfumery ingredients, such as aldehydes that are prone to oxidation, when put in contact with water under acidic conditions, may result in the formation of carboxylic acids, which, in turn, may lower the pH of the aqueous phase and cause gel weakening. If the gel is weakened, the perfume droplets may cream or sediment, especially when the system is exposed to elevated temperatures for a prolonged period of time.

As a precaution, therefore, it is desirable to add a buffer to the continuous phase having a pKa in the range of 4.0 to 9.0, more particularly 5.0 to 8.0, and still more particularly 6.0 to 8.0. It is also desirable the continuous phase should contain a base.

Buffers useful in the present invention may contain one or two sulphonic acid functions. Examples of suitable buffers include the phosphate buffers, 2-(N-morpholino) ethane sulphonic acid (MES), 2-amino-2-hydroxymethyl-1,3-propanediol, 2-(bis(2-hydroxyethyl)amino) acetic acid, 4-(2-hydroxyethyl)-1-piperazine ethane sulphonic acid (HEPES), sodium citrate and mixtures thereof.

In the context of the present invention, and unless stated otherwise, the term "phosphate buffer" means a buffer comprising dihydrogen phosphate ions and hydrogen phosphate ions.

A phosphate buffer according to the invention may be prepared by dissolving monosodium or monopotassium phosphate and disodium or dipotassium phosphate in water.

As phosphate buffer, we may mention PBS (phosphate buffered saline), prepared by dissolving disodium phosphate (10 mM), monopotassium phosphate (1.76 mM), sodium chloride (137 mM) and potassium chloride (2.7 mM) in water. PBS has a pKa of 7.2 and makes it possible to buffer an aqueous composition in a pH range from 6.5 to 7.9.

As phosphate buffer, we may also mention the buffer prepared by dissolving disodium phosphate (0.44 wt %) and monopotassium phosphate (2.74 wt %) in water. Such a buffer has a pKa of 5.8.

In particular, the buffer is 4-(2-hydroxyethyl)-1-piperazine ethane sulphonic acid, notably called HEPES (CAS No. 7365-45-9). HEPES has a pKa of 7.5 and makes it possible to buffer an aqueous composition in a pH range from 6.8 to 8.2.

According to one embodiment, the aqueous continuous phase of the dispersion comprises from 0.1 to 10 wt %, preferably from 0.5 to 5 wt % of buffer relative to the total weight of said aqueous continuous phase.

The aqueous continuous phase preferably comprises at least one base. It may therefore comprise a single base or a mixture of several different bases.

According to one embodiment, the base present in the aqueous phase is a mineral base.

According to one embodiment, the mineral base is selected from the group consisting of the hydroxides of the alkali metals and hydroxides of the alkaline-earth metals.

Preferably, the mineral base is an alkali metal hydroxide, and notably NaOH.

According to the invention, the dispersion of the invention may comprise from 0.01 to 10 wt %, preferably from 0.01 to 5 wt %, and more preferably from 0.05 to 1 wt % of base, preferably of mineral base, and notably of NaOH, relative to the total weight of the continuous phase.

According to the invention, among the organic bases, we may mention for example ammonia, pyridine, triethanolamine, aminomethylpropanol, or triethylamine.

There now follows a series of examples that further serves to illustrate the invention.

EXAMPLES

TABLE 1

| Raw materials | | |
| --- | --- | --- |
| Name | INCI Name | Supplier |
| Carbomer 340 FD | Carbomer | Evonik |
| Carbopol ® 981 | Carbomer | Lubrizol |
| Carbopol ® Aqua SF2 | Acrylates crosspolymer-4 | Lubrizol |
| KF8004 | Amodimethicone | Shin-Etsu |
| NaOH | Sodium Hydroxyde | Panreac |
| Microcare ® PE | Phenoxyethanol | Thor |
| Microcare ® Emollient PTG | Pentylene Glycol | Thor |
| Edeta ® BD | Disodium EDTA | BASF |
| Hepes | Hydroxyethylpiperazine Ethane Sulfonic Acid Hydro (HEPES) | Hopax |
| Perfume composition | Perfume | Givaudan |
| Dub Inin | Isononyl Isononanoate | Stearinerie Dubois |
| Deionized water | Aqua | — |

A series of perfume compositions, numbered 1 to 8 (below) are prepared according to the following procedure.

The external phase is prepared by dissolving the preservative agents Microcare PE and Edeta BD in the water for 15 minutes at 300 rpm mixing rate, using a dissolver-type propeller. Then the carbomer, the cross-polymer and the buffer system sodium hydroxide/HEPES are incorporated into the mixture and allowed to hydrate for one hour and finally dissolved rapidly, but without incorporating air bubbles, for two hours.

The internal phase is prepared by mixing the perfume composition and amodimeticone.

Isononyl isononaoate oil is added as intermediate phase stream.

The internal phase stream and the intermediate phase stream are incorporated in the external phase stream by using the micro-fluidic/milli-fluidic set up as described in US 2014/0045949.

The stream flow rates are given in Table 2

TABLE 2

Stream flow rates (the diluent of the external phase is deionized water q.s.p)

| Fluid | Composition | Rate (g/min) | wt % |
|---|---|---|---|
| Inner fluid | 99.5% Perfume 0.5% Amodimethicone | 3.97 | 9.48 |
| Middle Fluid | 100% DubInin | 0.4 | 0.96 |
| Outer Fluid | 0.25% Carbomer 1% Microcare ® PE 2.5% Microcare ® PTG 0.01% Edeta ® | 30 | 71.65 |
| Crosspolymer | 13.39% Acrylates crosspolymer-4 0.019% NaOH | 5.6 | 13.37 |
| Base | 4.81% NaOH 19.77% Hepes | 1.9 | 4.54 |

The final composition of the system is given in Table 3.

TABLE 3

System composition

| Raw material | INCI name | Concentration in system |
|---|---|---|
| Deionized water | Aqua | 83.72 |
| Perfume composition | Perfume | 8.91 |
| Oil | Isononyl isononaoate | 1.05 |
| Cationic coacervation precursor 1 | Amodimethicone | 0.050 |
| Anionic coacervation precursor 2 | Carbomer | 0.180 |
| Carbopol ® Aqua SF2 | Acrylates crosspolymer-4 | 1.800 |
| Microcare ® PE | Phenoxyethanol | 0.900 |
| Microcare ® Emollient PTG | Pentylene Glycol | 2.250 |
| Hepes | Hydroxyethylpiperazine Ethane Sulfonic Acid Hydro (HEPES) | 0.900 |
| Edeta ® BD | Disodium EDTA | 0.010 |
| NaOH | Sodium Hydroxyde | 0.230 |
| Total | | 100 |

The level of perfume composition in the perfume-containing droplet is 89 wt % and the overall perfume level in the system is 10 wt %.

The quality of the samples was assessed visually. The quality assessment criteria were: process feasibility, absence of drops coalescence, low drop coloration, absence of external gel phase whitening. The following nomenclature was used: "+"=good; "+/+"=acceptable and "−"=poor. The results are reported in Table 4.

TABLE 4

Results

| | Perfume composition # | | | | | | | |
|---|---|---|---|---|---|---|---|---|
| | 1 | 2 | 3 | 4 | 5 | 6 | 7 | 8 |
| Process feasibility | +/− | + | − | + | +/− | + | + | + |
| Drop coloration | − | +/− | | + | + | + | + | + |
| External phase whitening | − | − | | + | + | + | + | + |
| Droplet coalescence | − | + | | + | + | + | + | + |
| Total wt % terpene alcohols | 0.0 | 10.0 | 28.0 | 0.0 | 0.0 | 0.0 | 4.0 | 13.0 |
| Total wt % ingredients having ClogP <2.1 | 20.0 | 10.0 | 40.0 | 0.0 | 10.0 | 0.0 | 0.0 | 0.0 |
| Total wt % aldehydes | 80.0 | 5.0 | 0.0 | 0.0 | 5.0 | 0.0 | 0.0 | 0.0 |
| Overall quality assessment | − | +/− | − | + | +/− | + | + | + |

The results of Table 4 clearly demonstrate the interplay of the critical perfumery ingredients in determining the quality of the system.

The invention claimed is:

1. A perfume composition in the form of a plurality of dispersed perfume-containing droplets, suspended in an aqueous dispersing medium, said perfume droplets being mono-dispersed and having a diameter of 200 micrometers to 4000 micrometers, wherein said droplets comprise more than 60 wt of perfume ingredients, and wherein 25 wt % or less of said perfume ingredients are linear or branched alkyl alcohols and/or alkenyl alcohols; 10 wt % or less, of the perfume ingredients are aldehydes; and 10 wt % or less of the perfume ingredients have a ClogP less than 2.1, wherein said perfume composition comprises more than 60 wt % of perfume ingredients, and wherein 25 wt % or less of said perfume ingredients are linear or branched alcohols and/or alkenyl alcohols, 10 wt % or less of the perfume ingredients are aldehydes, and 10 wt % or less of the perfume ingredients have a ClogP less than 2.1, and wherein said perfume-containing droplets are coated with a layer of coacervate formed as the reaction product of an interaction between a first coacervate precursor polymer and a second coacervate precursor polymer, wherein said first coacervate precursor polymer is cationic, or capable of being ionised to form cations, and said second coacervate precursor polymer is anionic, or is capable of being ionised to form anions.

2. The perfume composition according to claim 1 which is free of or is substantially free of alcoholic or polar solvents.

3. The perfume composition according to claim 1 which is free of or is substantially free of surfactants.

4. The perfume composition according to claim 1, wherein the first coacervate precursor polymer is a silicone polymer modified with a primary, secondary or tertiary amine function.

5. The perfume composition according to claim 4, wherein the silicone polymer is amodimethicone.

6. The perfume composition according to claim 1, wherein the second coacervate precursor polymer is a crosslinked polymer or is a crosslinked copolymer, said polymer or copolymer comprising at least one unit derived from the polymerization of a monomer selected from the group consisting of acrylic acid, methacrylic acid, an alkyl acrylate comprising from 1 to 30 carbon atoms, and salts thereof.

7. The perfume composition according to claim 6, wherein the second coacervate precursor polymer is a carbomer and/or is a crosslinked acrylates/C10-30 alkyl acrylate copolymer.

8. The perfume composition according to claim 5, wherein the thickness of the coacervate coating is less than 1000 nm.

9. The perfume composition according to claim 1, wherein the aqueous dispersing medium comprises at least one cross-linked polymer and/or at least one cross-linked copolymer, comprising at least one unit derived from the polymerization of a monomer selected from acrylic acid, methacrylic acid, or salts thereof, and/or alkyl acrylate or methacrylate, the alkyl chain of said alkyl acrylate or methacrylate comprising 1 to 30 carbon atoms, or salts thereof.

10. The perfume composition according to claim 1, wherein the aqueous dispersing medium is a gel.

11. The perfume composition according to claim 1, wherein the aqueous dispersing medium comprises a buffer having a pKa in the range of 4.0 to 9.0.

12. The perfume composition according to claim 1, wherein the aqueous dispersing medium contains a base.

13. A method of preparing a perfume composition as defined in claim 1, wherein the method comprises the step of:

forming a plurality of dispersed perfume-containing droplets, suspended in an aqueous dispersing medium, said perfume-containing droplets being mono-dispersed and having a diameter of 200 to 4000 micrometers, wherein said droplets comprise more than 60 wt %, perfume ingredients, and wherein 25 wt % or less of said ingredients are linear or branched alkyl alcohols and/or alkenyl alcohols; 10 wt % or less of the perfume ingredients are aldehydes; and 10 wt % or less of the perfume ingredients have a clogP of less than 2.1.

14. A method of preparing a perfume composition as defined in claim 1, the method comprising the steps of:
  i) passing a mixture of the said perfume composition and a first coacervate precursor polymer through a first conduit; and
  ii) forming perfume-containing droplets of said perfume composition at the outlet of said first conduit, which outlet open into a second fluid comprising an aqueous continuous phase and a second coacervate precursor polymer that can interact with said first coacervate precursor polymer to form a coacervate which coats the droplets.

* * * * *